US007383358B1

(12) United States Patent
Kennedy

(10) Patent No.: US 7,383,358 B1
(45) Date of Patent: Jun. 3, 2008

(54) SYSTEM AND METHOD FOR REMOTE SERVICING OF IN-FIELD PRODUCT

(75) Inventor: Ronald G. Kennedy, Dousman, WI (US)

(73) Assignee: GE Medical Technology Services, Inc., Pewaukee, WI (US)

( * ) Notice: Subject to any disclaimer, the term of this patent is extended or adjusted under 35 U.S.C. 154(b) by 651 days.

(21) Appl. No.: 09/474,418

(22) Filed: Dec. 29, 1999

(51) Int. Cl.
*G06F 15/16* (2006.01)
(52) U.S. Cl. ...................................... 709/250
(58) Field of Classification Search ........ 709/217–225, 709/229, 250; 128/900, 920; 600/300; 705/1, 2, 7, 28; 379/15.03; 717/168, 171, 717/172, 173, 174; 205/2, 3
See application file for complete search history.

(56) References Cited

U.S. PATENT DOCUMENTS

| | | | | |
|---|---|---|---|---|
| 4,744,029 A | * | 5/1988 | Raviv et al. ................ 600/544 |
| 5,629,871 A | * | 5/1997 | Love et al. .................... 702/34 |
| 5,655,084 A | * | 8/1997 | Pinsky et al. .................. 705/3 |
| 5,678,562 A | * | 10/1997 | Sellers ....................... 600/523 |
| 5,687,717 A | * | 11/1997 | Halpern et al. ............. 600/300 |
| 5,715,823 A | * | 2/1998 | Wood et al. ................ 600/437 |
| 5,786,994 A | * | 7/1998 | Friz et al. ...................... 700/79 |
| 5,851,186 A | * | 12/1998 | Wood et al. ................ 600/437 |
| 5,867,821 A | * | 2/1999 | Ballantyne et al. ............. 705/2 |
| 5,897,498 A | * | 4/1999 | Canfield et al. ............ 600/437 |
| 5,938,607 A | * | 8/1999 | Jago et al. .................. 600/437 |
| 5,960,403 A | * | 9/1999 | Brown .......................... 705/2 |
| 6,138,249 A | * | 10/2000 | Nolet .......................... 714/25 |
| 6,168,563 B1 | * | 1/2001 | Brown ........................ 600/301 |
| 6,182,667 B1 | * | 2/2001 | Hanks et al. ................ 128/898 |
| 6,186,145 B1 | * | 2/2001 | Brown ....................... 128/897 |
| 6,225,901 B1 | * | 5/2001 | Kail, IV ................ 340/539.11 |
| 6,264,614 B1 | * | 7/2001 | Albert et al. ................ 600/528 |
| 6,278,999 B1 | * | 8/2001 | Knapp ........................... 707/9 |
| 6,306,089 B1 | * | 10/2001 | Coleman et al. ............ 600/437 |
| 6,325,540 B1 | * | 12/2001 | Lounsberry et al. ........ 378/114 |
| 6,325,759 B1 | * | 12/2001 | Pelissier ..................... 600/443 |
| 6,351,817 B1 | * | 2/2002 | Flyntz ........................ 713/202 |
| 6,353,445 B1 | * | 3/2002 | Babula et al. .............. 345/733 |

(Continued)

FOREIGN PATENT DOCUMENTS

WO WO 95/15521 * 6/1995

*Primary Examiner*—William Vaughn
*Assistant Examiner*—Yemane Mesfin
(74) *Attorney, Agent, or Firm*—Ziolkowski Patent Solutions Group, SC

(57) ABSTRACT

A system and method for remote servicing of an in-field product at a customer site. The remote servicing system includes a portable service interface, typically a laptop computer, which is utilized to connect a remote servicing on-line center with the in-field produce, such as a medical image scanner. The portable service interface includes software not resident with the in-field product to permit such servicing functions as diagnostic evaluations of the in-field product, as well as downloading configuration files, original source files, protocols and other software from the on-line center through the portable service interface at the customer site. The field engineer or other operator is able to provide service functions to in-field products that are not networked or are not readily networked with the on-line center and that do not have the on-line center connecting software resident on the portable service interface.

24 Claims, 2 Drawing Sheets

U.S. PATENT DOCUMENTS

| | | | |
|---|---|---|---|
| 6,356,780 B1 * | 3/2002 | Licato et al. | 382/128 |
| 6,375,614 B1 * | 4/2002 | Braun et al. | 600/300 |
| 6,385,593 B2 * | 5/2002 | Linberg | 705/28 |
| 6,393,380 B1 * | 5/2002 | Zemlo | 702/188 |
| 6,402,689 B1 * | 6/2002 | Scarantino et al. | 600/300 |
| 6,418,334 B1 * | 7/2002 | Unger et al. | 600/407 |
| 6,434,572 B2 * | 8/2002 | Derzay et al. | 707/104.1 |
| 6,440,071 B1 * | 8/2002 | Slayton et al. | 600/437 |
| 6,442,432 B2 * | 8/2002 | Lee | 607/59 |
| 6,471,087 B1 * | 10/2002 | Shusterman | 221/2 |
| 6,487,513 B1 * | 11/2002 | Eastvold et al. | 702/108 |
| 6,496,099 B2 * | 12/2002 | Wang et al. | 340/3.7 |
| 6,519,632 B1 * | 2/2003 | Brackett et al. | 709/219 |
| 6,524,245 B1 * | 2/2003 | Rock et al. | 600/437 |
| 6,564,104 B2 * | 5/2003 | Nelson et al. | 607/60 |
| 6,579,231 B1 * | 6/2003 | Phipps | 600/300 |
| 6,665,820 B1 * | 12/2003 | Frowein et al. | 714/43 |
| 6,694,367 B1 * | 2/2004 | Miesbauer et al. | 709/227 |

* cited by examiner

SYSTEM AND METHOD FOR REMOTE SERVICING OF IN-FIELD PRODUCT

BACKGROUND OF THE INVENTION

The present invention relates generally to remote servicing of in-field products or equipment, and more particularly, to a system and method for remote servicing of in-field product connecting a centralized on-line service center to the in-field product, such as medical diagnostic equipment, through a portable service interface.

Medical diagnostic equipment and supporting systems, such as medical imaging systems, have become increasing complex in recent years. Examples of such systems include magnetic resonance imaging (MRI) systems, computed tomography (CT) systems, ultrasound and x-ray systems, and positron emission tomography (PET) systems. To add to the complexity of each particular imaging system, many facilities today incorporate a variety of such equipment. In larger facilities, the systems may be networked to permit common management and control. Further, such systems may be networked with a picture archiving and communication system (PACS) for storing digitized image data for subsequent retrieval and reconstruction. Additionally, teleradiology, systems involve transmitting digitized image data to remote locations for review and diagnosis by specialized physicians and/or radiologists.

Because medical diagnostic systems are critical elements in the diagnosis and treatment of patients, their use must not be inhibited by a slow response for service or maintenance. Due to the increasing complexity of these systems, trained service personnel are oftentimes not on location with the equipment. Therefore, remote servicing of medical diagnostic equipment has become an important tool in maintaining these systems.

Remote servicing of medical diagnostic equipment has traditionally been performed via voice communication between operations personnel and a centralized servicing facility. Operations personnel would call a remote service facility to report malfunctions and ask questions regarding the proper operation and settings for the equipment. When such queries could not be sufficiently handled by telephone, a service or field engineer was dispatched to troubleshoot the system and provide the needed assistance.

Improvements in computer networks have greatly facilitated the task of offering assistance to medical imaging equipment. In particular, rather than having to call a service center and talking to a technician or engineer, or having to await a return call from the service center, network technologies have facilitated proactive techniques wherein the service center may contact the medical diagnostic equipment to check the status of subscribing equipment. Further advancements have been proposed to provide remote service to medical diagnostic systems in an effort to provide the level of service on a continual and interactive basis as needed by many facilities. In one such system, a service center can interactively receive messages via a network and can respond automatically to the messages if configured correctly. Data required to analyze the state of operation of the medical diagnostic equipment can be transferred during an electronic connection. This technique greatly facilitates identification of system problems, allows questions to be posed to the subscribing service provider, facilitates transfer of updates and imaging protocols, and permits standard and customized reports to be transmitted to subscribing systems or stations. The interactive aspect of this technique allows the medical diagnostic facility to remain current on services provided by the centralized service facility and to readily communicate with the centralized service facility.

While such advancements in the provisions of remote services to medical diagnostic equipment has greatly enhanced the level of service and information exchange, such advancements can only be taken advantage of by systems that are networked to the service center. Non-externally networked medical diagnostic equipment, or systems without interactive service software resident on the in-field product at the customer site may not be able to receive service or use resources of the service center due to the inability to connect or communicate with the centralized service facility. Typically, a field engineer at the customer site can get additional phone support by calling the on-line service center and talking to the one of the support engineers. However, without a mechanism to access or interface with the remote servicing center, the level of service available to a medical diagnostic system decreases significantly, with the field engineer or technician having to rely upon more traditional remote servicing techniques.

In present systems that are networked to an on-line service center, the on-line service center will dial up the particular system by way of a phone line and connect to the in-field product via a modem that is resident at the customer system in order to access the system. However, for non-networked systems, there is a need to directly connect the in-field product to the on-line service center to allow the field engineers to utilize current service tools in order to bridge a customer system with the on-line service center. Such a system would be particularly useful for systems that do not have the requisite communication software to connect to the on-line service center directly.

It would therefore be desirable to have a system and technique for the remote servicing of the in-field product that can communicate with diagnostic medical systems that do not have the application software that allows for communication with the remote resources such as the on-line service center. It would also be advantageous to have a system that utilizes service tools that are already widely used by field support personnel. It would also be advantageous to have a system that could receive diagnostic evaluations and data from the on-line center, even with a non-networked system.

SUMMARY OF THE INVENTION

The present invention provides a system and method for remote servicing an in-field product by utilizing a portable service interface as a connection between an on-line center and an in-field product that overcomes the aforementioned problems.

In one aspect of the invention, a remote servicing communications system for an in-field product is disclosed. The system includes at least one on-line center having access to service software at a centralized facility so as to service in-field products remotely. The system also includes an in-field product at a customer site that is not readily capable of direct communication with the on-line center. At least one portable service interface is operable with the in-field product at the customer site and has a software for communication with the on-line center. The system includes a first communications link connecting the portable service interface to the on-line center, and a second communications link connecting the portable service interface with the in-field product. In this manner, there is a connection between the in-field product and the on-line center through the portable service interface.

Accordingly, the present invention also includes a method for providing a remote service communication between an on-line center and in-field product at a customer site where the in-field product is not readily capable of direct communication with the on-line center. The method includes loading on-line center conductivity software onto a portable service interface and connecting the portable service interface to the in-field product. After such a connection is accomplished, the method includes electronically connecting the on-line center with the portable service interface and accessing data from the in-field product through the portable service interface, such that interfacing between the on-line center and the in-field product may begin. The interfacing step may include transmitting data about the in-field product to the on-line center for the purpose of evaluating the in-field product and generating in-field product evaluation information. This information is then displayed on the portable service interface. The interfacing step may also include accessing data from the on-line center including configuration files, original incorruptible source of "golden" files, protocols or other software.

According to another aspect of the invention, the invention includes a method of servicing an in-field product not readily capable of direct communication with a remote on-line center. The method includes providing a portable service interface having software for communication with the on-line center, and connecting the portable service interface to the in-field product. Upon electronically connecting the on-line center with the portable service interface, the method includes selecting at least one servicing function available from the on-line center. This is followed by interfacing the in-field product with the on-line center through the portable service interface to conduct diagnostic evaluation of the in-field product or downloading information to the in-field product from the on-line center through the portable service interface. Finally, the method includes displaying the diagnostic evaluation or downloaded information on the portable service interface at the customer site as a result of the selecting step.

Various other features, objects and advantages of the present invention will be made apparent from the following detailed description and the drawings.

BRIEF DESCRIPTION OF THE DRAWINGS

The drawings illustrate the best mode presently contemplated for carrying out the invention.

In the drawings.

DETAILED DESCRIPTION OF THE PREFERRED EMBODIMENT

Figure 1:
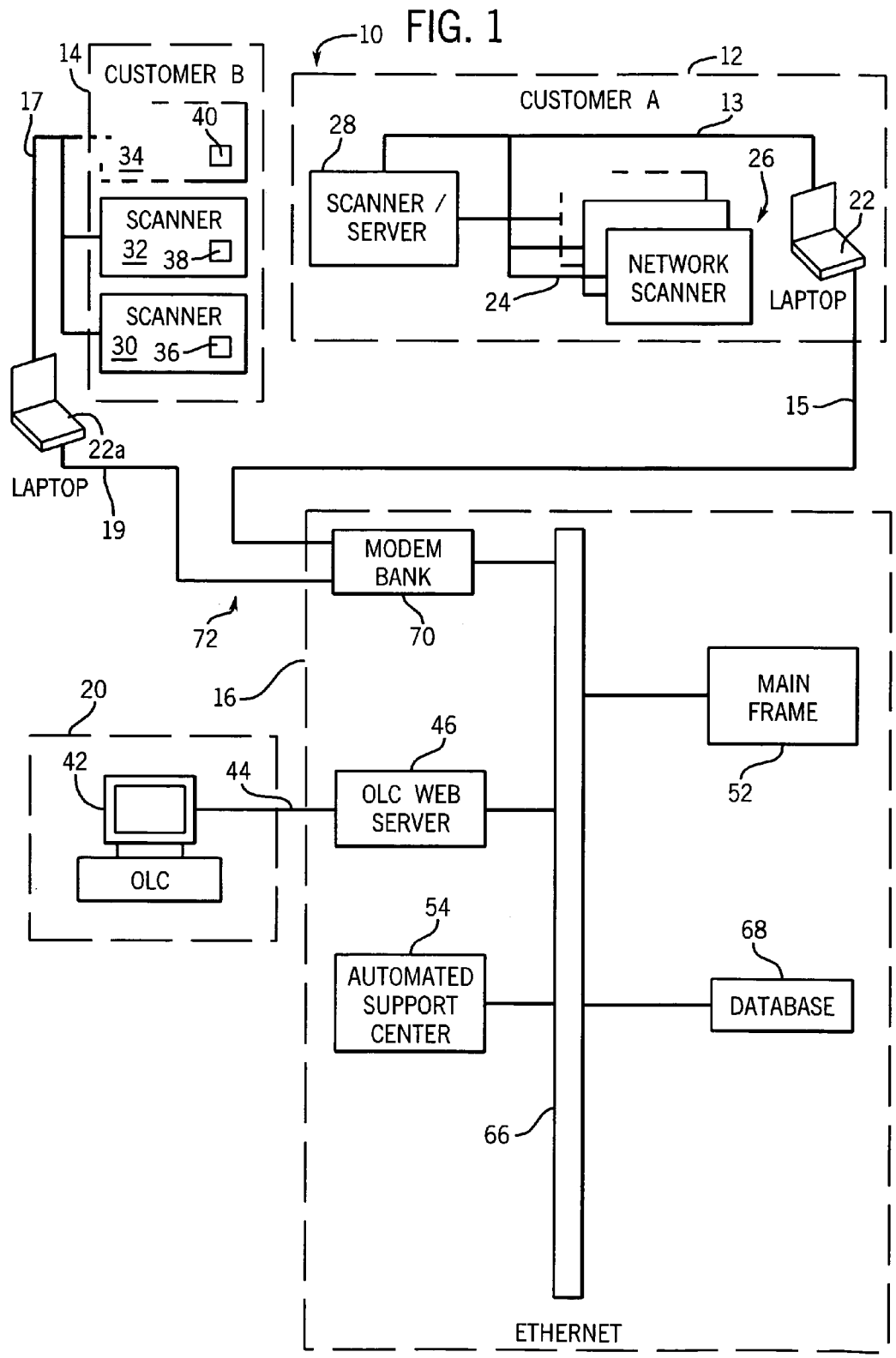
FIG. 1 is a schematic block diagram of a system incorporating the present invention.

Referring to FIG. 1, an overview block diagram of a medical diagnostic and service system 10 is shown which includes a plurality of stations, such as Customer A referenced with numeral 12, and Customer B referenced with numeral 14. It is understood that the number of stations can be limitless, but two specific embodiments are shown with Customer A and Customer B, which will be further explained hereinafter. The various systems disclosed are configured to be selectively linked to an on-line center 16 by a portable service interface, preferably a laptop computer 22-22a, configured with appropriate connectivity and diagnostic interface software, although any portable service tool that is capable of bridging the on-line center 16 with one of the systems 12, 14 is contemplated by the present invention. Although a single on-line center is shown and described, it is understood that the present invention contemplates the use of multiple on-line centers, each capable of communication with each station. The stations 12, 14, are connected to the on-line center 16 through a communications link 15, 19 which are connected to each portable service interface 22-22a. Such selective linking is desirable to provide upgrades, maintenance, service, and general monitoring of the various systems and equipment at a customer site, which includes accessing data from the systems and transmitting data to the systems, for example.

In general, a customer site, or subscribing station, may have a number of in-field products, such as medical image scanners. Also, the subscribing stations may include a variety of medical diagnostic systems of various modalities. As an example, in the present embodiment, the in-field products may include a number of internally networked medical image scanners 26 connected to an internal network 24 served by a single scanner 28 having a work station configured to also act as a server, or configured as a stand-alone server without a medical image scanner associated therewith. Alternately, a subscribing station, or customer site 14 can include a number of non-internally networked in-field products such as medical image scanners, 30, 32, 34, each having a computer or work station associated therewith and having an internal modem 36, 38, 40 to facilitate the portable service interfaces 22-22a connecting each station 12, 14, to communications links 15, 19 to ultimately communicate with the on-line center 16. As an alternative to a direct dial-up link, communications can be through an Internet connection. Each portable service interface or laptop 22-22a has remote servicing communications software associated therewith through which the in-field products 26, 30, 32, 34 can be configured, evaluated, serviced, maintained, upgraded, or simply monitored by the on-line center 16, which also has access to service software to service in-field product remotely. It is not necessary in the present invention that the in-field product be absolutely incapable of communication with the on-line center. The present invention contemplates such cases as where an in-field product at a customer site may have the necessary hardware, but because of, for example, termination of servicing contracts, the servicing software is not available to the individual in-field product. Therefore, the laptop 22 provides the necessary servicing and communications software that may have been removed as a result of the expiration of servicing contracts. Additionally, the communications between the portable service interface and the on-line center may be accomplished by a single phone line, or a bank of modems 70 through a portmaster at the on-line center or other connection network.

The laptops or other portable service interfaces 22-22a are required since they are the only locations at the customer site where the software for connecting to the on-line center 16 resides. The in-field products at the particular customer sites for which the invention is applicable lack specific connectivity software which would normally provide the on-line center 16 with the ability to dial up the medical image scanners or other in-field products in order to conduct the desired on-line remote servicing function. Absent this capability, the systems are considered non-networked with the on-line center, and therefore require a bridge or interface, such as the portable service interfaces 22-22a, to make the desired connections.

In the Customer A system 12, the laptop 22 is connected to the internally networked scanners by a communication link connection 13, which preferably is a network cable, such as a local access network cable, so that the laptop 22 or other portable service interface may interact with each of the scanners 26 within the local network, by sending and receiving data. It is understood that each of the network scanners 26 has its own workstation for individual operation and are linked together by the internal network 24 so that the customer can have a centralized management system for each of the scanners. The laptop 22 is also connected via communications link or telephone connection 15 to a modem or Internet link 72 to the on-line center 16. Therefore, the laptop 22 is the sole electronic connection for Customer A between its network scanners 26 and the on-line center 16. Similarly, the laptop 22*a* for Customer B in system 14 is connected to each individual scanner by communications link 17, which is preferably a serial connection cable. The laptop 22*a* is also connected via a telephone connection 17 and via a modem or other communications link 19, which may or may not utilize an Internet Protocol (IP) based system, in order to connected with the on-line center 16. Again, the laptop 22*a* provides the sole electronic connection or bridge between the scanners 30, 32, 34 of Customer B and the on-line center 16. Without the laptops 22, 22*a* and their installed connectivity software, such on-line remote servicing connections would not be possible. Although FIG. 1 shows each of these communications links 15, 19 connected through a dedicated network, in another embodiment, it is understood that these links can permit data to be transferred to and from the systems over an open network, such as the Internet as well.

The embodiment shown in FIG. 1 contemplates a medical facility having such systems as magnetic resonance imaging (MRI) systems, ultrasound systems, x-ray systems, computed tomography (CT) systems, as well as positron emission tomography (PET) systems, or any other type of medical imaging system. Such facilities may also provide services to centralized medical diagnostic management systems, picture archiving and communications systems (PACS), teleradiology systems, etc. Such systems can be either stationary and located in a fixed place and availably by a known network address, or be mobile having various network addresses. In the embodiment shown in FIG. 1, each customer station 12, 14 can include any combination of the aforementioned systems, or a station may have all of one type of a system. A customer station can also include a single medical image scanner. Mobile diagnostic systems can be configured similarly to that of station 12 or station 14. Such mobile diagnostic systems can include equipment of various modalities, such as MRI, CT, ultrasound, or x-ray systems and are mobilized in order to better service various medical facilities and patients.

The communications between the on-line center and the in-field product of the present invention can be initiated by authorized personnel, such as a field engineer or technician, an on-line engineer or technician, administrative personnel, and/or other such similar authorized personnel, from a laptop computer 22 connected to a customer internal network 24, or from the laptop computer 22*a* individually connected to each of the scanners 30, 32, or 34. Similarly, the system can be initialized by a computer or workstation 42 in the remote link 20, which can be a part of the on-line center 16, or be separately connected to the on-line center 16 a dialup link 44 to a web server 46 in the on-line center 16. The on-line center 16 includes a number of processing systems including a mainframe computer 52, an automated support center 54 and the web server 46, for processing customer and product data, creating appropriate configuration files, and selecting service software based on an identification signal received from a subscribing station that identifies the medical image scanner. The processing systems are connectable and can transmit data to one another through a network such as an ethernet 66, or with at least one database 68. It is understood that the single representation of a database in FIG. 1 is for demonstrative purposes only, and it is assumed that there is a need for multiple databases in such a system. A bank of modems 70 is connected to the ethernet 66 to relay data from the on-line center 16 and to the subscribing stations 12, 14 through a plurality of modem links 72 to the portable service interfaces 22-22*a*.

As previously discussed, each of the systems and substations described herein and referenced in FIG. 1 may be linked selectively to the on-line center 16 via a network 15, 19. According to the present invention, any acceptable network may be employed whether open, dedicated, virtual private, or so forth. Further, the communications link to the network may be of any acceptable type, including conventional telephone lines, cable modem links, digital subscriber lines, and the like. Each of the portable service interfaces 22-22*a* is provided with communications interface hardware and software, permitting them to establish network links and exchange data with the on-line center 16. With the present invention, the portable service interfaces 22-22*a* are provided with interactive software so as to configure the systems and exchange data between the stations and the on-line center 16.

In operation, the field engineer or other service personnel would take the portable service interface, or in this case the laptop 22, 22*a*, connect it to a communications link such as telephone connection 15, 19 at, for example, a hospital where the in-field product would reside or other customer site, and then connect the laptop 22, 22*a* to the network port or serial port via communications links 13, 17 on the particular customer's system. The laptops 22, 22*a* then act as the bridge or interface between the on-line center and the customer in-field products. The portable service interface sends a data message to the on-line center identifying the medical image scanner. The on-line center then selects service software, which resides on the laptop, based on the medical image scanner's identification and can, if needed, automatically download the selected service software to the medical image scanner. It is understood that the term "service software" includes, but is not limited to, software updates, repair software, diagnostic software, data files, or any other electronic files for use with a particular in-field product. The on-line center can the perform a desired function, such as diagnostic evaluations, upgrading software, downloading files, protocols or other software from the on-line center. In some cases, it may be desirable to download certain "golden" files, which are source code files which are compiled and known at the on-line center to be an uncorrupted file, and that are in a secure location such that they cannot be corrupted. Therefore, such original source files if desired may be downloaded through the laptops 22, 22*a* and into the customer systems. Although the above-enumerated functions are preferred, it is contemplated that any remote resource functions that are suitable for transmission from the on-line center to the customer site are contemplated by the present invention. The goal is to provide the customer with the opportunity to have an on-line support engineer at the on-line center, through the field engineer's laptop 22-22*a*, and provide real time assistance and information for the particular scanner of interest.

Figure 2:
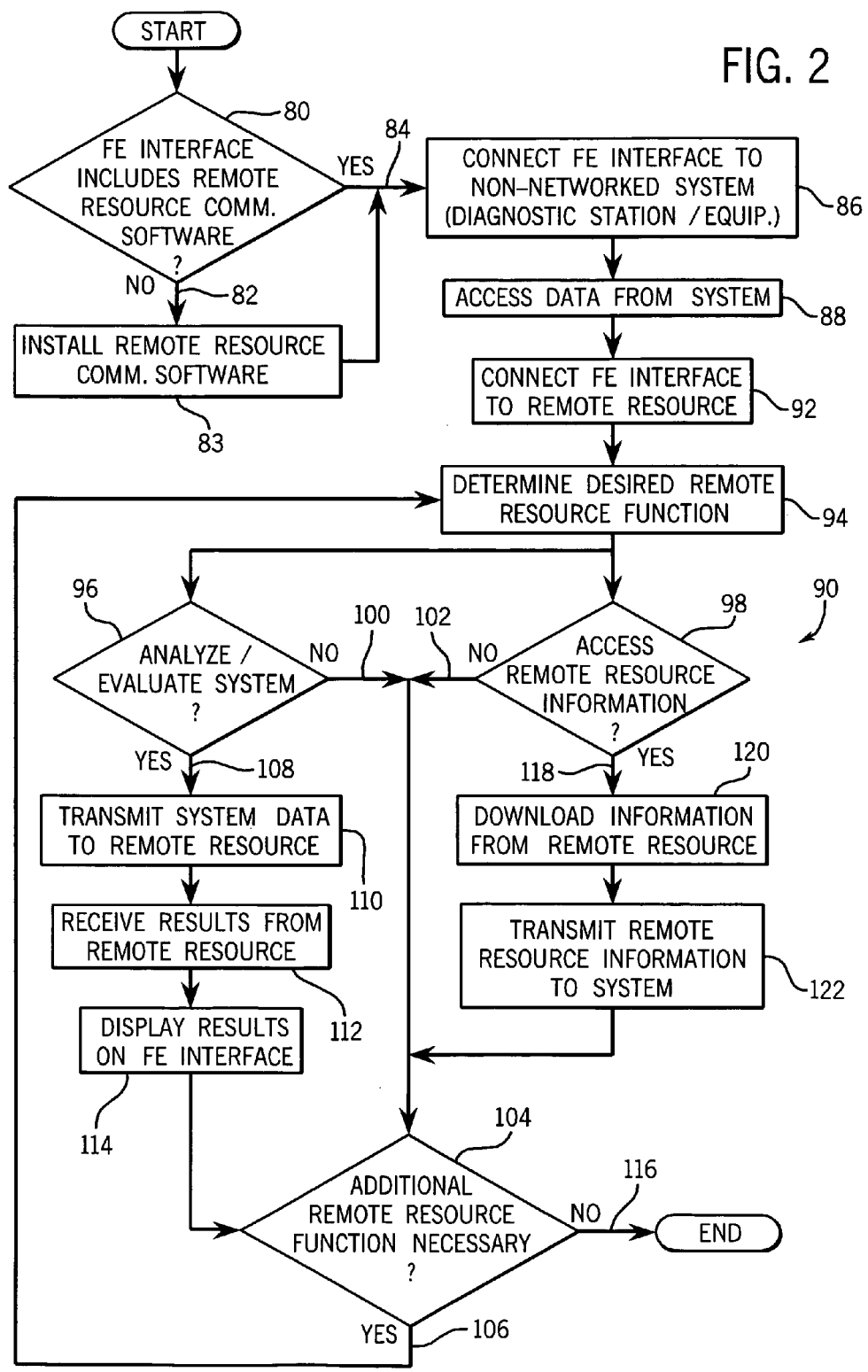
FIG. 2 is a flow chart of the process of the present invention as incorporated in the system of FIG. 1.

FIG. 2 shows a process flow chart incorporating and overviewing the present invention. Each of the aforementioned components, referred to in FIG. 1, are specifically designed to enable connections initiating by a field engineer, or from the remote link 20. In a preferred embodiment, the on-line center includes network servers and server software designated to provide for interactive exchange of data via the network link. Such servers may be based on any known or suitable software or protocol for exchanging data. For example, such protocol can include the point-to-point protocol (PPP) employing Internet protocol (IP) packets, hypertext transfer protocol (HTTP), or any other data exchange means. Preferably, the servers are designed to process and transfer raw data or processed data, such as image data processed into a standard format. Finally, the servers are preferably equipped to support HTTP applications and include a browser capable of displaying interactive pages, such as those found in HTML, XTL, or other language configurations, and to support JAVA applications, applets, servlets, and similar code for carrying out the functional details of a browser and as described herein.

Referring to FIG. 2 in more detail, the initial check 80 is performed to determine whether the portable service interface or field engineer (FE) interface includes the remote resource communication software which will allow communication with the on-line center 16 or other remote resource. If not 82, the remote source communication software is installed 83 on the portable service interface. If the FE interface already has the software 84, then the portable service interface is properly equipped to accompany the field engineer to a customer site, such as on a service request. While at the customer site, the field engineer connects the portable service interface to the non-networked system 86. By non-networked, it is meant that the system does not have the communication software or hardware to network with the on-line center. After this connection is made, it is possible to access data 88 from the system or system network if the medical diagnostic scanner is part of a local access network. The portable service interface is then able to be utilized as a remote resource interface 90 by providing a connection from the portable service interface to the remote resource 92 such as the on-line center. This connection may be made to the on-line center by the software on the laptop or portable service interface dialing a preprogrammed number through a phone line connecting to the on-line center. Alternately, the portable service interface can connect to the on-line center through a global network system, such as the Internet. The connection may also be made by the field engineer providing a telephone number and/or IP address to the on-line center, with the on-line center initiating the connection with the field engineer's laptop.

After the connection to the remote resources made, it is then necessary to determine which remote resource function is desired 94. A check is made to determine whether it is desired to analyze and evaluate the system for diagnostic purposes 96. A check is also made to determine whether it is desired to access information such as software, protocols, specific files and the like from the remote resource 98. Other checks may be made for other desired service functions. If it is not desired to analyze and evaluate the system 102 or if it is not desired to access information from the remote resource 100, the system determines whether additional resource functions are necessary 104. If analysis and/or evaluation is desired 96, 108, data is transmitted to the remote resource 110 and diagnostic evaluation results and analysis are received from the remote resource 112 with the results being on the field engineer portable service interface 114. If no additional remote resource functions are necessary 104, 116, the process is complete. If the FE desires access to remote resource information 118, that information is downloaded 120 from the remote resources and transmitted 122 from the remote resource to the non-networked system. Following this, the system checks to determine whether additional remote resources functions are necessary 104. If not additional resources are required 116, the process is complete.

The present invention is designed to promote remote servicing communication between in-field product and an on-line service center through a portable service interface. Accordingly, the invention includes a method of servicing an in-field product not readily capable of direct communication with a remote on-line center. The method includes providing a portable service interface having software for communication with the on-line center, and connecting the portable service interface to the in-field product. Upon electronically connecting the on-line center with the portable service interface, the method includes selecting at least one servicing function available from the on-line center. The in-field product is then interfaced with the on-line center through the portable service interface to conduct diagnostic evaluation of the in-field product or downloading information or software to the in-field product from the on-line center. The method optionally includes displaying the diagnostic evaluation or downloaded information on the portable service interface at the customer site as a result of the selecting step.

The invention also includes a remote service and communication system for in-field products. The system includes at least one on-line center having access to service software at a centralized facility so as to service in-field product remotely. The service software can include upgrade software, replacement software, repair software, system documentation and related data, or any other type of electronic data useful to the in-field product. The system includes an in-field product located at a customer site that is typically not readily capable of direct communication with the on-line center. A portable service interface is operable with the in-field product at the customer site and has software for communication with the on-line center. A first communications link is provided to connect the portable service interface to the on-line center and a second communication link connects the portable service interface with the in-field product to complete a connection between the in-field product and the on-line center through the portable service interface.

In one application, the connection between the in-field product and the on-line center is used to conduct diagnostic evaluation of the in-field product. In a preferred embodiment, the in-field product is a medical image scanner and the on-line center contains many different versions and types of service software designed for utilization with a wide range of medical image scanners. After the portable service interface sends a data message identifying the medical image scanner, the on-line center selects service software based on the medical image scanner identification and automatically downloads the selected service software to the medical image scanner or executes the needed software from the portable service interface. The portable service interface can be a laptop computer having loaded therein remote resource communications software to automatically communicate with the on-line center and transfer files, or data, therebetween.

The present invention has been described in terms of the preferred embodiment, and it is recognized that equivalents, alternatives, and modifications, aside from those expressly stated, are possible and within the scope of the appending claims.

The invention claimed is:

1. A remote servicing communication system for in-field product comprising:
   at least one on-line center having access to service software at a centralized facility so as to service in-field product remotely;
   an in-field product at a customer site that is not readily capable of direct communication with the on-line center;
   at least one portable service interface operable with the in-field product at the customer site and having software for communication with the on-line center;
   a first communications link connecting the portable service interface to the on-line center; and
   a second communications link connecting the portable service interface with the in-field product to complete a connection between the in-field product and the on-line center through the portable service interface.

2. The system of claim 1 wherein the connection between the in-field product and the on-line center is utilized to conduct a diagnostic evaluation of the in-field product.

3. The system of claim 1 wherein the in-field product is a medical image scanner and the on-line center contains service software designed for utilization with a wide variety of medical image scanners, and wherein after the portable service interface sends a data message identifying the medical image scanner, the on-line center selects service software based on the medical image scanner identification and automatically downloads the selected service software to the medical image scanner or executes the selected service software from the portable service interface.

4. The system of claim 1 wherein the connection between the in-field product and the on-line center is utilized to access data from the on-line center.

5. The system of claim 4 wherein the accessed data from the on-line center includes at least one of a configuration file, a golden file, a protocol and a software program.

6. The system of claim 1 wherein the portable service interface sends a data message signal to the on-line center identifying the in-field product such that the on-line center selects service software specifically designed for the in-field product.

7. The system of claim 1 wherein the second communication link connecting the portable service interface to the in-field product is one of a serial cable and a local area network cable.

8. The system of claim 1 wherein the portable service interface is a laptop computer having loaded therein remote resource communications software to automatically communicate with the on-line center and transfer data therebetween.

9. The system of claim 1 wherein the connection to the on-line center provides access to a remote on-line support engineer to provide real time assistance with the in-field product through the portable service interface.

10. A method of providing remote service communication between an on-line center and an in-field product at a customer site wherein the in-field product is not readily capable of direct communication with the on-line center comprising:
    loading on-line center connectivity software on a portable service interface;
    connecting the portable service interface to the in-field product;
    electronically connecting the on-line center with the portable service interface;
    accessing data from the in-field product with the portable service interface; and
    interfacing between the on-line center and the in-field product with the portable service interface.

11. The method of claim 10 further comprising the steps of transmitting data identifying the in-field product to the on-line center for evaluating and servicing the in-field product, and automatically selecting service software at the on-line center, and generating in-field product evaluation information and displaying the in-field product evaluation information on the portable service interface.

12. The method of claim 10 wherein the interfacing step includes accessing data from the on-line center including at least one of a configuration file, a golden filed, a protocol and a software program.

13. The method of claim 10 wherein the in-field product is a medical image scanner and further comprises automatically selecting at the on-line center service software based on a specific identification of the medical image scanner.

14. The method of claim 10 further comprising the step of automatically checking whether a field service engineer requests an analysis/evaluation, and if so, transmitting system data to the in-field product and performing an analysis/evaluation of the in-field product.

15. The method of claim 14 further comprising displaying results of the analysis/evaluation so that the field service engineer can monitor the analysis/evaluation.

16. The method of claim 10 wherein the connecting step further includes connecting the portable service interface to the in-field product by one of a serial cable and a local area network cable.

17. The method of claim 10 further comprising the steps of automatically checking to see whether a field service engineer requests access to remote resource information, and if so, downloading the remote resource information to the in-field product.

18. The method of claim 17 further comprising the step of displaying a remote resource information to the in-field service engineer.

19. The method of claim 10 wherein the electronically accessing step occurs through a global computer network system.

20. The method of claim 10 wherein the electronically connecting step further includes providing access to a remote on-line support engineer to provide real time assistance with the in-field product through the portable service interface.

21. A method of servicing an in-field product not readily capable of direct communication with a remote on-line center comprising:
    providing a portable service interface having software for communication with an on-line center;
    connecting the portable service interface to the in-field product;
    electronically connecting the on-line center with the portable service interface;
    from the portable service interface, selecting at least one servicing function available from the on-line center resulting in at least one of the following:

(A) interfacing the in-field product with the on-line center through the portable service interface to conduct a diagnostic evaluation of the in-field product; and (B) downloading information to the in-field product from the on-line center through the portable service interface; and displaying one of the diagnostic evaluation and the downloaded information on the portable service interface as a result of the selecting step.

22. The method of claim 21 wherein the in-field product is a medical image scanner and further comprising the steps of transmitting a data message identifying the medical image scanner from the portable service interface to the on-line center, automatically selecting service software at the on-line center based on the medical image scanner identification, and automatically downloading the selected service software to the medical image scanner.

23. The method of claim 21 further comprising the steps of automatically checking whether a field service engineer requests an analysis/evaluation, and if so, transmitting system data to the in-field product and performing an analysis/evaluation of the in-field product, and displaying results of the analysis/evaluation so that the field service engineer can monitor the analysis/evaluation.

24. The method of claim 21 further comprising the steps of automatically checking to see whether a field service engineer requests access to remote resources information, and if so, downloading the remote resource information to the in-field product, and displaying a remote resource information to the in-field service engineer.

* * * * *